United States Patent [19]
Kristiansen

[11] 4,183,240
[45] Jan. 15, 1980

[54] METHOD AND APPARATUS FOR DETECTING PLY SEPARATIONS IN CARCASSES

[75] Inventor: Oddvar Kristiansen, Gjøvik, Norway
[73] Assignee: Svenska Sio Maskin AB, Karlstad, Sweden
[21] Appl. No.: 860,513
[22] Filed: Dec. 14, 1977
[51] Int. Cl.² ............................................. G01N 25/00
[52] U.S. Cl. ...................................... 73/15 R; 73/146
[58] Field of Search .................. 23/15 R, 15.4, 146, 23/160

[56] References Cited

U.S. PATENT DOCUMENTS

| | | | |
|---|---|---|---|
| 2,909,060 | 10/1959 | Branick | 73/146 |
| 3,664,188 | 5/1972 | Kockott | 73/150 |

FOREIGN PATENT DOCUMENTS

847287 9/1960 United Kingdom ........................ 73/15

OTHER PUBLICATIONS

Barendsz et al., "A Heating Rate Controller for Accelerated Storage Tests" in J. of Physics E, vol. 9, #2, pp. 129–131.

*Primary Examiner*—Herbert Goldstein
*Attorney, Agent, or Firm*—Pollock, Vande Sande & Priddy

[57] ABSTRACT

Method of detecting ply separations in carcasses comprising the steps of entering the carcasses into a drying chamber, heating the carcasses to a temperature of about 100°–130° C., discharging the carcasses from the drying chamber and inspecting them in respect to visible deficiencies and apparatus for carrying out said method comprising a drying chamber in shape of an elongated tunnel, a conveyor for advancing the aforestated carcasses through the tunnel, an airduct connecting the inlet end of the tunnel with the outlet end thereof, the airduct including a fan for recycling a stream of air through the tunnel in a direction opposite to the direction of advance of the carcasses and a heating means to heat the air stream.

3 Claims, 1 Drawing Figure

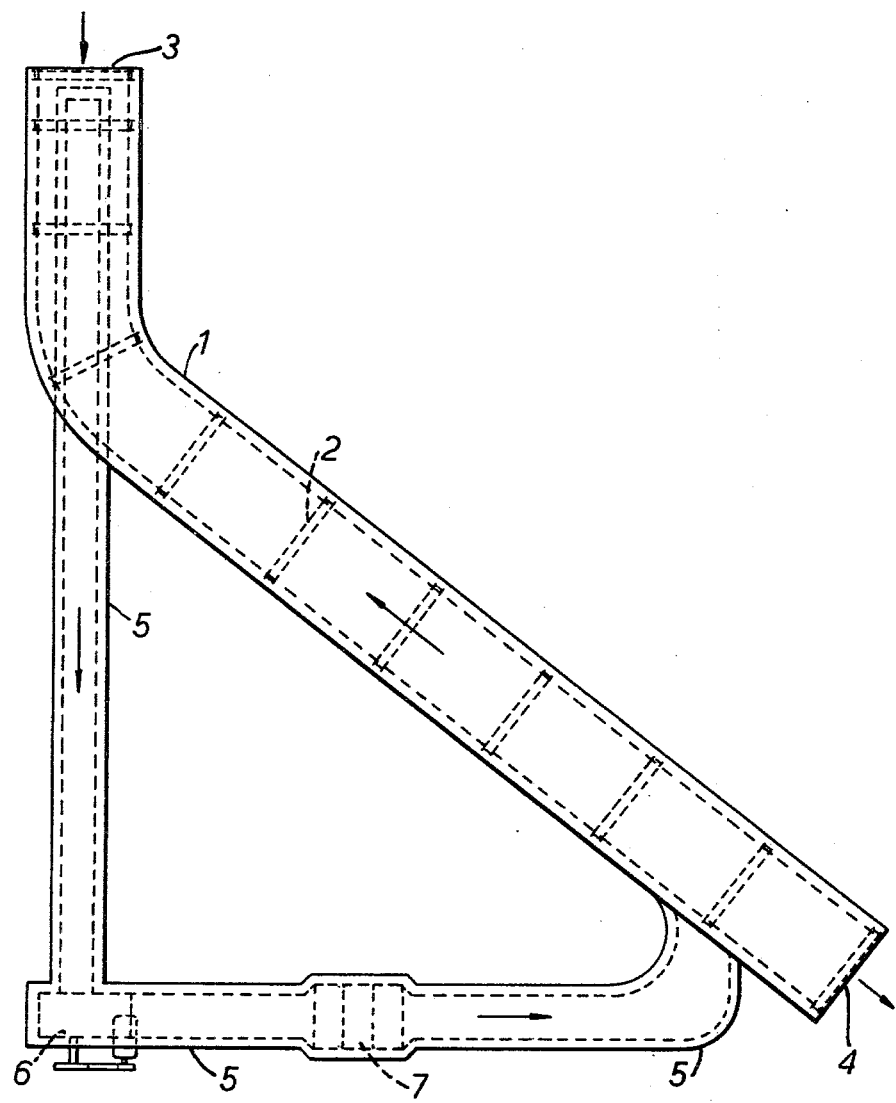

METHOD AND APPARATUS FOR DETECTING PLY SEPARATIONS IN CARCASSES

BACKGROUND OF THE INVENTION

The present invention relates to a method and an apparatus for detecting ply separations and other deficiencies in carcasses prior to the retreading thereof.

It is of great importance to carefully inspect all used vehicle tires in respect to ply separations and other deficiencies before they are retreaded, since otherwise, many of the finished tires have to be rejected. In most of the present retreading plants there exists and excessively high percentage of rejection or cassation, which is due to the fact that all deficiencies are not discovered during the inspection of the tires or carcasses carried out prior to their retreading. In many instances, such deficiencies become visible only during the proper retreading process wherein such deficiencies are greatly magnified. The most common deficiency is the ply separations which become visible only after heating.

The first step of the retreading process usually consists of heating and drying the carcasses in a drying chambwer for example, in which they are heated to about 60°–80° C. for a day and night or more to remove inherent moisture. After the heating and drying treatment the carcasses are moved through an inspection device for detecting present deficiencies such as ply separations. The heating operation carried out in the above manner has proven unsatisfactory in failing to reveal all ply separations, resulting in the excessive amount of rejected retreaded tires.

OBJECTS AND SUMMARY OF THE PRESENT INVENTION

The primary object of the present invention is to reduce the percentage of cassation of retreaded tires by heating the used tires or carcasses to a temperature of about 100°–130° C. in a drying chamber, whereby any ply separation is distinctly noticable during the inspection procedure immediately following the drying operation, so that carcasses including ply separations may be rejected to avoid retrading thereof. The carcasses are preferably advanced by a conveyor throught an elongated drying chamber or tunnel, wherein the carcasses are heated and dryed for about 40 to 70 minutes dependent on the temperature of the heating medium, which preferably may be in the range of 110°–140°. The heating medium may consist of air containing vapour so as to reduce the danger of explosion of the inflammable gas developed from tires at increased temperatures of 100°–130° C.

The apparatus of the present invention comprises a drying chamber in which used vehicle tires are heated by a gaseous medium such as air, and a means for heating the gaseous medium. According to the invention the drying chamber is an elongated tunnel having an inlet at one of its ends and an outlet at the other end and a conveyor for advancing the carcasses throught the tunnel. A separate gas conduit connects the inlet end of the tunnel with the outlet end thereof. The heating means is disposed in said conduit as well as a fan which is adapted to recirculate the gas flow through the conduit and tunnel in a direction opposite to the direction of advance of the carcasses in the tunnel.

The accompanying drawing and the following description will further illustrate and embodiment of the present invention.

The drawing illustrates a schematic elevational view of the apparatus of the present invention which is disposed upstream of the conventional retreading device (not shown). The apparatus consists of a tunnel 1 extending horizontally in a suitable manner depending on the local space situation. A conveyor, e.g. a roll conveyor having rolls 2, extends through the tunnel 1 and is adapted to carry batches or piles of carcasses or used tires to advance them successively through the tunnel 1. Carcasses to be retreaded enter the tunnel 1 through an inlet door 3 and are discharged through an outlet door 4. An air conduit 5 leads from the inlet door 3 through a fan 6 and one or more vapour batteries 7 to the outlet zone of the tunnel 1. The fan 6 draws the air from the inlet end of the tunnel and generates a recirculating air flow in the direction of the arrows opposite to the direction of advance of the carcasses in the tunnel 1. The outlet end of the conduit opening into the tunnel 1 is accordingly bent in a direction opposite to the direction of advance of the carcasses. The air is heated by the vapour batteries 7 or other suitable heating means.

The apparatus operates in the following manner: Carcasses or used tires to be retreaded enter the tunnel 1 through the inlet door 3 and advance stepwise in batches or piles through the tunnel 1 toward the outlet door 4. In the conduit 5 the fan 6 generates an air stream which is heated by the vapour batteries 7 to a temperature of about 110°–140° C. The air flows in a direction opposite to the direction of advance of the carcasses in the tunnel 1 thereby to heat them to a temperature of 100°–130° C. before they are discharged through the outlet door 4. As soon as they leave the tunnel 1 the carcasses are transferred to a conventional inspection device, where they are inspected with respect to deficiencies such as ply separations. Owing to the increased temperature (about 100°–130° C.) of the carcasses substantially all separations will clearly present themselves at the inspection device so that defective carcasses could be rejected before transferring the flawless ones further to the proper retreading machine.

The present invention thus provides for (a) a fast and improved drying of the carcasses (about 1 hour as compared to one or several days in the drying chambers used heretofore);
(b) a quicker and more accurate inspection of the carcasses (inherent separations otherwise impossible to detect clearly present themselves. Blisters and nail holes are easily discovered);
(c) a more rational handling;
(d) a significant reduction of the cassation percentage of retreaded tires (from about 15% to 2%) which means great economic savings).

The invention is not limited to the above discribed embodiment but could be modified within the scope of the following claims.

What is claimed is:

1. A method of detecting deficiencies such as ply separations in tire carcasses prior to retreading said carcasses, comprising the following steps:
    entering and advancing said tire carcasses through a tunnel-like passageway;
    directing a stream of hot gases through said passageway;
    heating said tire carcasses within said passageway to a temperature in the range of substantially 110°–130° C. to remove moisture from said carcasses as well as to magnify inherent deficiencies in said carcasses;

removing said tire carcasses from said tunnel-like passageway and inspecting said carcasses for deficiencies.

2. A method according to claim 1, including the further step of:

directing a stream of hot gases through said tunnel-like passageway in a direction opposite to the direction of movement of said tire carcasses through said tunnel-like passageway.

3. A method according to claim 1, including the further step of:

directing a stream of hot air in the temperature range of substantially 110°–140° C. through said passageway for heating said tire carcasses advancing therethrough, and recycling said air stream through an air duct extending between opposite end portions of said passageway.

* * * * *